(12) United States Patent
Holden et al.

(10) Patent No.: US 9,719,938 B2
(45) Date of Patent: Aug. 1, 2017

(54) IDENTIFICATION OF MATERIAL TYPE AND CONDITION IN A DRY BULK MATERIAL HOPPER

(71) Applicant: Halliburton Energy Services, Inc., Houston, TX (US)

(72) Inventors: Kristin Katherine Holden, Fletcher, OK (US); Robert Paul Freese, Pittsboro, NC (US)

(73) Assignee: HALLIBURTON ENERGY SERVICES, INC., Houston, TX (US)

(*) Notice: Subject to any disclaimer, the term of this patent is extended or adjusted under 35 U.S.C. 154(b) by 0 days.

(21) Appl. No.: 15/508,893

(22) PCT Filed: Oct. 28, 2014

(86) PCT No.: PCT/US2014/062579
§ 371 (c)(1),
(2) Date: Mar. 3, 2017

(87) PCT Pub. No.: WO2016/068868
PCT Pub. Date: May 6, 2016

(65) Prior Publication Data
US 2017/0184508 A1  Jun. 29, 2017

(51) Int. Cl.
*G08B 21/18* (2006.01)
*G01N 21/85* (2006.01)
(Continued)

(52) U.S. Cl.
CPC ......... *G01N 21/85* (2013.01); *G01N 21/8806* (2013.01); *G01N 21/94* (2013.01); *G01N 23/02* (2013.01); *G01N 2021/8592* (2013.01)

(58) Field of Classification Search
CPC ............... G01N 21/85; G01N 21/8507; G01N 21/8528; G01N 21/88; G01N 21/8806;
(Continued)

(56) References Cited

U.S. PATENT DOCUMENTS 8,141,695 B2    3/2012  Kraus et al.
2004/0031335 A1*  2/2004  Fromme ................ G01B 11/24
                                           73/865

(Continued)

FOREIGN PATENT DOCUMENTS

JP    08-067315 A    3/1996
JP    08-172895 A    7/1996
JP    2013-224196 A  10/2013

OTHER PUBLICATIONS

International Search Report and Written Opinion dated Jul. 14, 2015, which issued in international Application No. PCT/US2014/062579.

*Primary Examiner* — Van Trieu
(74) *Attorney, Agent, or Firm* — McDermott Will & Emery LLP

(57) ABSTRACT

A method includes optically interacting a bulk material or powder stored in a hopper with an integrated computational element ("ICE") configured to detect a characteristic of the bulk material or powder. The method also includes generating an output signal corresponding to the characteristic of the bulk material or powder, and receiving and processing the output signal with a signal processor to yield a value for the characteristic of the bulk material or powder. Also, the method includes transmitting a message flagging the hopper when it is determined that the bulk material or powder is not suitable for usage.

23 Claims, 7 Drawing Sheets

(51) Int. Cl.
*G01N 21/94* (2006.01)
*G01N 21/88* (2006.01)
*G01N 23/02* (2006.01)

(58) Field of Classification Search
CPC ............... G01N 21/94; G01N 21/945; G01N 2021/8835; G01N 2021/8841; G01N 2021/8887; G01N 23/02; G01N 23/12
See application file for complete search history.

(56) References Cited

U.S. PATENT DOCUMENTS

| | | | |
|---|---|---|---|
| 2005/0246088 A1* | 11/2005 | Doherty | ............... E01H 10/007 701/80 |
| 2008/0178734 A1 | 7/2008 | Butler et al. | |
| 2016/0258269 A1* | 9/2016 | Musso | ............... E21B 47/0005 |

* cited by examiner

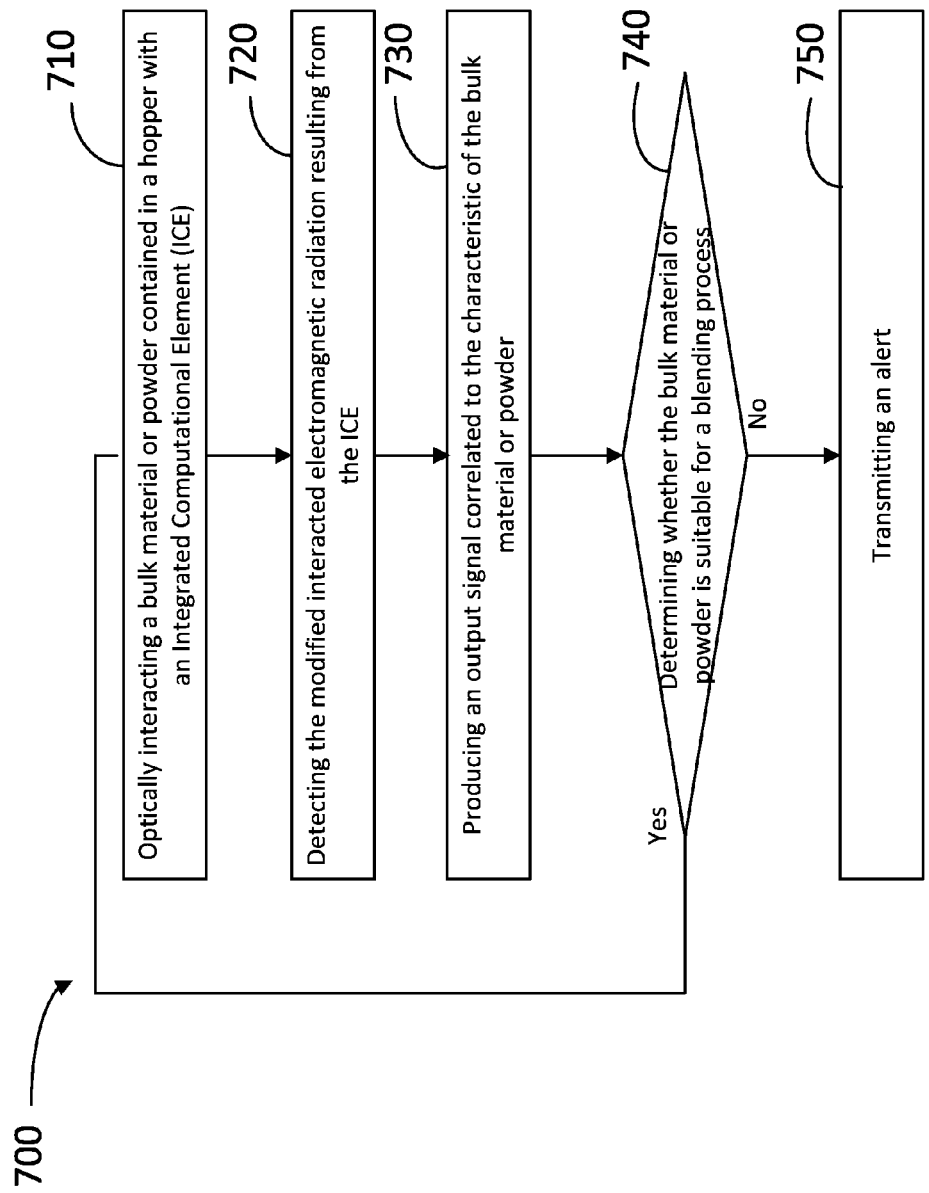

IDENTIFICATION OF MATERIAL TYPE AND CONDITION IN A DRY BULK MATERIAL HOPPER

BACKGROUND

The exemplary embodiments described herein relate to optical analysis systems and methods for measuring characteristics of a dry bulk material or powder. More particularly, embodiments disclosed herein relate to systems and methods for measuring the characteristics of a bulk material or powder in storage and use the measurements to improve the characteristics and ensure the quality of blends including the bulk material or powder.

Some industrial applications that use bulk materials and powders include forming set cement compositions for the construction industry. The oil and gas industry also uses set cement compositions for stabilizing and plugging wellbores, among other purposes. The operational parameters relating to cement slurries and the characteristics of the resultant set cement derive, at least in part, from the dry cement composition and the composition and concentration of the optional cement slurry additives mixed as powders in the dry cement blend composition.

Accordingly, while storing and conveying raw materials used in a blend to form a dry cement, it is desirable to have a correct determination of the raw materials used and their physical and chemical condition during storage and transfer. It is also desirable to determine flow conditions in a conveying system to optimize energy costs and to avoid damage to the infrastructure for handling the materials. Current techniques include discrete measurements in storage containers and pipelines at specific locations and times. Other techniques involve imprecise and unreliable methods such as detecting the sound that the raw material makes as it travels through the pipelines. Other approaches include analyzing the discharge of the raw material at the end or at some intermediate point of the pipeline.

These measurement techniques typically involve a complicated, multi-step process of mixing harsh chemicals with the bulk materials or powders and analyzing the products via expensive, time-consuming methods like x-ray diffraction, gravimetric analysis, slurrying and testing viscosity over time in specified temperature and pressure conditions, and the like. Moreover, these measurement techniques may be insufficient for taking remedial action when an error occurs with one or more of the material supplies and an entire batch of dry cement is lost or deployed on location without satisfying quality standards. In relation to downhole oil and gas operations, improperly deployed cementing operations can increase both costs and liabilities, including costly remedial operations to repair the set cement.

BRIEF DESCRIPTION OF THE DRAWINGS

The following figures are included to illustrate certain aspects of the exemplary embodiments described herein, and should not be viewed as exclusive embodiments. The subject matter disclosed is capable of considerable modifications, alterations, combinations, and equivalents in form and function, as will occur to those skilled in the art and having the benefit of this disclosure.

FIG. 7 illustrates a flowchart including steps in a method for identification of material type and condition in a bulk material or powder stored in or flowing through a hopper, according to some embodiments.

DETAILED DESCRIPTION

Figure 1:
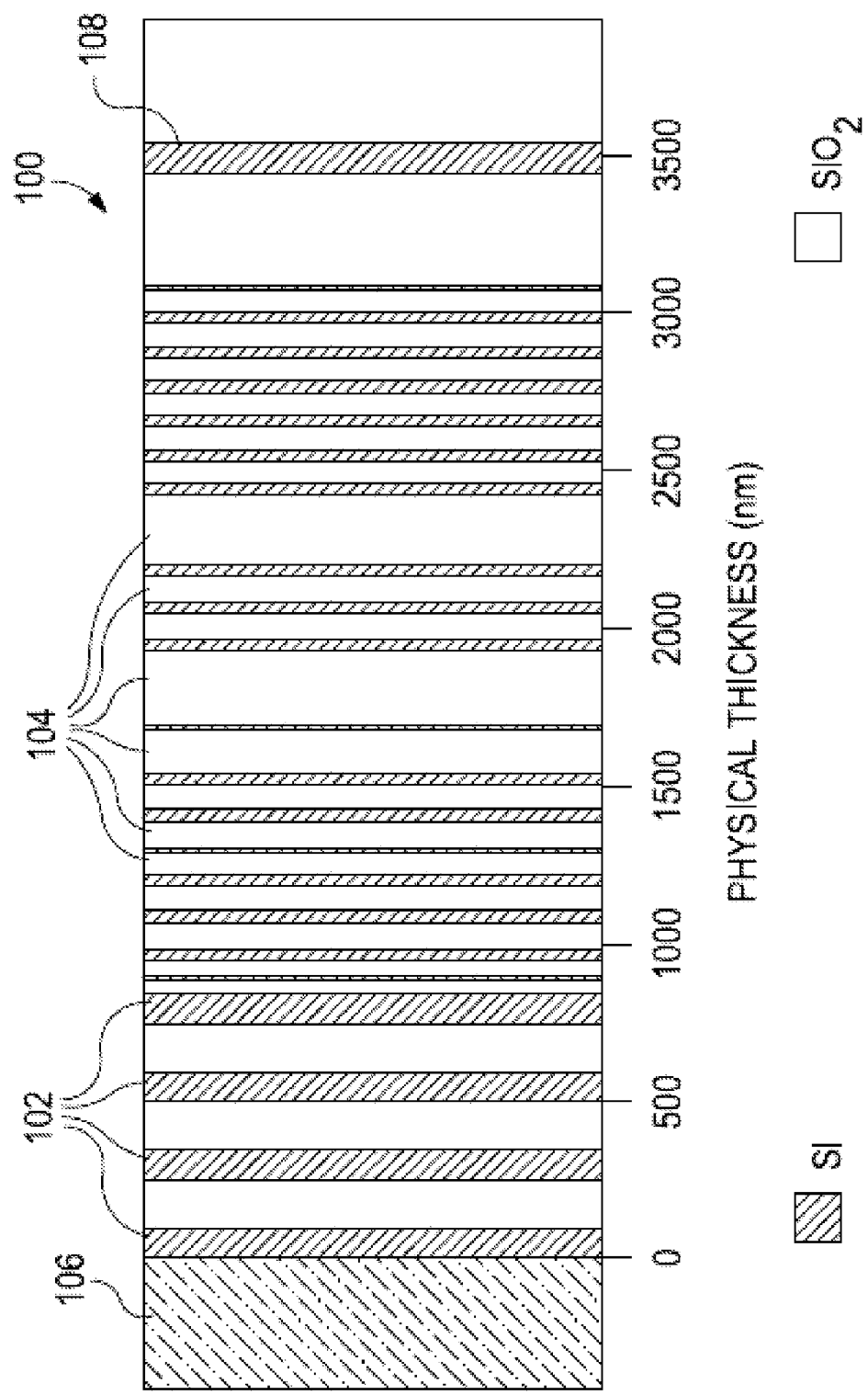
FIG. 1 illustrates an exemplary integrated computational element (ICE), according to one or more embodiments.

The exemplary embodiments described herein relate to optical analysis systems and methods for monitoring bulk materials or powders and, in particular, to systems and methods for determining the characteristics and condition of bulk materials or powders. Methods and systems consistent with the present disclosure are able to characterize the flow by "seeing" the bulk materials or powders as they are stored for use in a conveying and blending system in real time. Accordingly, methods and systems consistent with the present disclosure enable adjustment of conveying and blending procedures based on the characteristics of the stored bulk materials or powders.

Many industrial applications commonly use dry bulk materials and powders. For example, the agro-industry, the food industry, and the pharmaceutical industry process large amounts of grains, powders, liquids and small unit sizes (fruits such as grapes, raisins, and nuts, medications in the form of pills) for storage, packaging, and distribution. Industrial applications of dry bulk materials or powders include storing separated raw materials under dry conditions prior to mixing and preparation for use. Industrial applications of dry bulk materials typically include systems and methods to store the raw materials in separate containers for each raw material and conveying mechanisms to transport the raw materials from storage containers to a scale tank and from the scale tank to a shipping location, or a deployment location. At each of the storage and conveying stages, it is desirable to have a precise knowledge of the type and physical condition of the material handled. Some of the characteristics that are relevant in many applications include powder particle size, moisture content, homogeneity of a mixture, and flow conditions in a conveying system.

The oil and gas industry uses bulk materials and powders for making cement blends deployed for example, to plug boreholes or secure casing strings therein. Some of these cementing projects may be quite challenging, as it may be desirable to convey a cement composition beyond the ocean floor, several thousand feet underneath the water surface. Accordingly, it is desirable to verify the correct dry cement blend prior to deploying the cement in the field. The oil and gas industry uses many types of cements according to different desirable characteristics for specific applications. In some instances, dry cements include any one of the raw materials used in Portland cements, gypsum cements, hydraulic cements and Sorel cements. Other dry materials besides dry cement typically used in the oil and gas industry include salt, lime, sand, POZMIX®, and the like. An accurate account of the identity and condition of the raw materials used to prepare the cement mix during storage and conveying of the raw materials is therefore highly desirable. In some instances, the physical condition is relevant to reactivity of the raw material in cement slurries. For example, fines (reduced size particles) react differently from coarser particles of the same material. Moreover, coarse materials have a tendency to settle and deposit in storage containers and transfer tubes before arriving to the desired destination, reducing material transfer efficiency. Furthermore, blending conditions may change in time, and thus it is desirable to have a sense of the condition of the bulk material or powder being used in real time, and adapt the blending methodology accordingly.

Current attempts to obtain information about bulk material or powder identity and condition include sample extraction and analysis on a periodical basis at multiple locations. These methods can be time consuming and discrete in nature, providing partial and extemporaneous information that may not be sufficient for a timely remedial action. Thus, when an error occurs in the supply logistics and the wrong material is used, or pipeline corrosion contaminates the sample or the mixture, or an air pump or compressor leaks moisture into the system, an entire batch of the mix may be compromised. This may result in the loss of the batch, or in a worst-case scenario, more serious damage can occur when the wrong batch is deployed in the field. Such may be the situation when a compromised cement mix is used in structural engineering, such as plugging or lining a wellbore extending from the sea bed, thousands of feet under water.

The exemplary systems and methods described herein employ various configurations of optical computing devices, also commonly referred to as "opticoanalytical devices," for the rapid analysis of dry cements. The disclosed systems and methods may be suitable for use in the oil and gas industry since the described optical computing devices provide a cost-effective, rugged, and accurate means for identifying bulk materials and powders in order to facilitate the effective production of cement slurries and set cements in oil/gas applications. It will be appreciated, however, that the various disclosed systems and methods are equally applicable to other technology fields including, but not limited to, the food and drug industry, industrial applications, mining industries, or any field where it may be advantageous to determine in real-time or near real-time a characteristic of a dry composition, especially to determine the quality of the dry composition and of each of its components.

The optical computing devices disclosed herein, which are described in more detail below, can advantageously provide rapid analysis of at least one characteristic of a dry cement (e.g., the composition of individual components in the dry cement or the particle size distribution in the dry cement). As described above, such a detailed analysis currently requires extensive time, high cost, and harsh chemicals and can give unreliable results. By contrast, the optical computing devices disclosed herein may provide rapid analysis of dry cements with minimal sample prep, if any. Additionally, because the analysis is rapid, multiple measurements may be obtained to reduce error. Further, because of the small size and relatively low cost of the optical computing devices disclosed herein, the methods for analyzing dry cements are suitable not only for laboratory use, but also, in-field analysis (e.g., at a manufacturing or mining site, at a distribution center, or at a well site).

A significant and distinct advantage of the optical computing devices disclosed herein is that they can be configured to specifically detect and/or measure a particular characteristic of interest of a dry cement, thereby allowing qualitative and/or quantitative analyses of the material of interest to occur without having to undertake a time-consuming sample processing procedure. With rapid analyses capabilities on hand, the exemplary systems and methods described herein may be able to determine the identity and flow characteristics of raw materials used to form dry cement compositions.

As used herein, the term "dry cement" refers to a mixture of solid particles including at least some cement particles and is not hydrated beyond ambient conditions (e.g., no additional water has been added). It should be noted that the term "dry cement" does not refer to set cements (e.g., that have been formed from a cement slurry).

Dry cements may comprise a single cement or comprise a blend of two or more cements. Examples of dry cements may include, but are not limited to, hydraulic cements, Portland cement, gypsum cements, pozzolan cements, calcium phosphate cements, high alumina content cements, silica cements, high alkalinity cements, shale cements, acid/base cements, magnesia cements (e.g., Sorel cements), zeolite cement systems, cement kiln dust cement systems, slag cements, micro-fine cements, bentonites, and the like, any derivative thereof, and any combination thereof. Examples of Portland cements may include, but are not limited to, Portland cements classified as Classes A, C, H, and G according to API and their equivalent, Ordinary Portland cements of Type I, I/II, III, and V according to ASTM, including combinations thereof. Examples of pozzolan cements may include, but are not limited to, fly ash, silica fume, granulated blast furnace slag, calcined shale, opaline shale, pumice, pumicite, diatomaceous earth, volcanic ash, tuft, cement kiln dust, and any combination thereof.

As used herein, the term "characteristic" refers to a chemical, mechanical, or physical property (quantitative or qualitative) of a material of interest (e.g., a dry cement or an analyte thereof). As used herein, the term "analyte" refers to a chemical component. The term analyte encompasses chemical components that are at least one of: present in the material of interest, may be added to the material of interest, involved in a chemical reaction (e.g., reagents and products) transpiring within the material of interest, and not involved in a chemical reaction transpiring within the material of interest. Illustrative characteristics of a material of interest that can be monitored with the optical computing devices disclosed herein can include, for example, chemical composition (e.g., identity and concentration in total or of individual analytes), contaminant content, pH, viscosity, density, ionic strength, salt content, porosity, opacity, bacteria content, particle size distribution, color, temperature, hydration level, oxidation state, and the like. Moreover, the phrase "characteristic of interest" may be used herein to refer to a characteristic of a material of interest.

Examples of analytes within a dry cement may include, but are not limited to, $SiO_2$, $Al_2O_3$, $FeO$, $Fe_2O_3$, $CaO$, $Na_2O$, $K_2O$, $MgO$, $SO_3$, $Mn_2O_3$, $TiO_2$, $P_2O_5$, $SnO$, $SrO$, $(CaO)_3.SiO_2$, $(CaO)_2.SiO_2$, $(CaO)_3.Al_2O_3$, $(CaO)_3.Al_2O_3.Fe_2O_3$, $CaSO_4.H_2O$, $SO_3$, $Ca(OH)_2$, $Al(OH)_4^-$, $H_4SiO_4$, free lime, inorganic salts (e.g., sodium, potassium, magnesium, and calcium salts of sulfate, phosphate, and carbonate), metal containing compounds (e.g., bromide, chloride, nitrate, sulfate, and phosphate salts of cadmium, zinc, nickel, copper, lead, and the like, metal oxides of such metals, and the like), hydroxides, water, and any combination thereof.

In some instances, the foregoing analytes may be used in classifying cements (i.e., as a major component) or as grading cements (i.e., as a minor components), which depends on the dry cement. As used herein, the "major component" of a dry cement refers to a component or analyte that identifies the type of dry cement (e.g., Portland cement versus Sorel cement or Type I Portland cement versus Type V Portland cement). As used herein, the "minor component" of a dry cement refers to a component or analyte that is not a major component. The terms "major component" and "minor component" do not necessarily relate to a concentration. For example, in Ordinary Grade, Class G Portland cement may have about 5% $CaO_3.Al_2O_3$ as one of the major components and up to about 6% MgO as one of the minor components.

As used herein, the term "cement slurry additive" refers to an additive that can be included in cement slurries with water and dry cements. Cement slurry additives may be liquids or dry additives (e.g., powders). In some instances, the dry cement and at least one cement slurry additive (typically a dry additive) form a mixture used in preparing cement slurries. The mixture may be prepared at a storage facility, manufacturing facility, laboratory, distribution center, at the well site, or in transit between any of these locations.

Examples of cement slurry additives may include, but are not limited to, set retarders, set accelerators, fillers (e.g., weighting agents, lightweight particles like glass beads, rubber particles, and the like), dispersants, gelling agents, and the like, and any combination thereof.

As used herein, the term "electromagnetic radiation" refers to radio waves, microwave radiation, infrared and near-infrared radiation, visible light, ultraviolet light, X-ray radiation and gamma ray radiation.

As used herein, the term "optical computing device" refers to an optical device that receives an input of electromagnetic radiation from a substance or sample of the substance, and produces an output of electromagnetic radiation from a processing element arranged within the optical computing device. The processing element may be, for example, an integrated computational element (ICE) used in the optical computing device. As discussed in detail below, the ICE optically interacts and changes the electromagnetic radiation incident on a detector such that an output of the detector can be correlated to at least one characteristic of the substance being measured or monitored. The output of electromagnetic radiation from the processing element can be reflected electromagnetic radiation, transmitted electromagnetic radiation, and/or dispersed electromagnetic radiation. Whether the detector analyzes reflected or transmitted electromagnetic radiation may depend on the structural parameters of the optical computing device as well as other considerations known to those skilled in the art. In addition, emission and/or scattering by the substance, for example via fluorescence, luminescence, Raman scattering, and/or Raleigh scattering, can also be monitored by the optical computing devices.

As used herein, the term "optically interact" or variations thereof refers to the reflection, transmission, scattering, diffraction, or absorption of electromagnetic radiation either on, through, or from one or more processing elements (i.e., integrated computational elements). Accordingly, optically interacted light refers to electromagnetic radiation that has been reflected, transmitted, scattered, diffracted, or absorbed by, emitted, or re-radiated, for example, using the integrated computational elements, but may also apply to interaction with a dry cement.

The exemplary systems and methods described herein will include at least one optical computing device configured to measure at least one characteristic of a dry cement or analyte thereof. In some embodiments, the optical computing devices suitable for use in the exemplary embodiments described herein may be mobile or portable. In some embodiments, the optical computing devices suitable for use in the exemplary embodiments described herein may be a portion of tank, silo, vat, pipeline, tube, or the like that store, mix, transfer or otherwise contain or transport dry cement (e.g., within a wall).

The presently described optical computing devices combine the advantage of the power, precision, and accuracy associated with laboratory spectrometers, while being extremely rugged and suitable for field use. Furthermore, the optical computing devices can perform calculations in real-time or near real-time without the need for time-consuming sample processing. In this regard, in some embodiments the optical computing devices detect and analyze particular characteristics of interest. As a result, interfering signals are discriminated from those of interest by appropriate configuration of the optical computing devices, such that the optical computing devices provide a rapid response regarding the characteristic of interest as based on the detected output. In some embodiments, the detected output is a voltage indicative of the magnitude of the characteristic of interest. The foregoing advantages and others make the optical computing devices particularly well suited for field use.

In some embodiments, the optical computing devices detect not only the composition and concentrations of an analyte in a material of interest, but also determine physical properties and other characteristics of the material of interest as well, based on their analysis of the electromagnetic radiation received from the substance. For example, the optical computing devices can determine the concentration of an analyte and correlate the determined concentration to a characteristic of the material of interest by using suitable processing means. In some embodiments, optical computing devices as disclosed herein provide a measurement of a granularity of a powder sample, or an average particle size in the powder sample. As will be appreciated, the optical computing devices can detect as many characteristics as desired for a given material of interest. All that is required to accomplish the monitoring of multiple characteristics of interest is the incorporation of suitable processing and detection means within the optical computing device for each characteristic of interest (e.g., the concentration of an analyte, the particle size distribution, or the temperature). Another property of a dry cement that can be measured may be the particle size of the different components in the cement.

In some embodiments, the properties of the material of interest can be determined using a combination of characteristics of interest (e.g., a linear, non-linear, logarithmic, and/or exponential combination). Accordingly, the more characteristics detected and analyzed using the optical computing devices, the more accurately the properties of the material of interest will be determined. For example, properties of a dry cement that may be determined using optical computing devices described herein may include, but are not limited to, the absolute concentration of an analyte, the relative ratios of two or more analytes, the presence or absence of an analyte, and the like, and any combination thereof.

Optical computing devices as described herein utilize electromagnetic radiation to perform calculations, as opposed to the hardwired circuits of conventional electronic processors. When electromagnetic radiation interacts with a material of interest, unique physical and chemical information about the material of interest may be encoded in the electromagnetic radiation that is reflected from, transmitted through, or radiated from the material of interest. This information is the spectral "fingerprint" of the material of interest. The optical computing devices described herein are capable of extracting the information of the spectral fingerprint of multiple characteristics of a material of interest (e.g., a dry cement blend or an analyte thereof), and converting that information into a detectable output regarding the overall properties of the monitored material of interest. That is, through suitable configurations of the optical computing devices, electromagnetic radiation associated with characteristics of interest can be separated from electromagnetic radiation associated with all other components of the material of interest in order to estimate the properties (e.g., reactivity) of the monitored substance (e.g., a dry cement blend or an analyte thereof) in real-time or near real-time.

Each of the ICEs used in the exemplary optical computing devices described herein is capable of distinguishing electromagnetic radiation related to the characteristic of interest from electromagnetic radiation related to other components of a dry cement blend.

A method according to some embodiments includes optically interacting a bulk material or powder contained in a hopper with an integrated computational element ICE configured to modify an electromagnetic radiation according to a characteristic of the bulk material or powder. The method also includes detecting the modified electromagnetic radiation with a detector, and producing an output signal with a signal processor. The output signal is correlated with the characteristic of the bulk material or powder. The method further comprises determining whether the bulk material or powder is suitable for a blending process. In some embodiments, the method includes transmitting an alert when it is determined that the bulk material or powder is not suitable for the blending process. The bulk material or powder comprises at least one of a dry cement, a dry cement component, or an analyte of interest. Bulk materials or powders as disclosed herein may include not only dry cement, but also may include dry barite powders and blends used for drilling fluids. More generally, bulk materials or powders as disclosed herein include dry powders and blends such as fertilizer, pharmaceuticals and agro-industrial products.

A device according to some embodiments includes a processor circuit and a memory circuit storing commands. When executed by the processor circuit the commands cause the device to perform a method including receiving a first signal from a first optical computing device at a first location in a system for storing and conveying materials. The commands also cause the device to perform the step of receiving a second signal from a second optical computing device at a second location in the system for storing and conveying materials. In some embodiments, the first and second signals result from an electromagnetic radiation interacted with a dry cement component contained in a hopper, and at least one of the first and second signals results from an electromagnetic radiation modified by an Integrated Computational Element (ICE) according to a characteristic of the dry cement. The commands also cause the device to perform the steps of determining a characteristic of the dry cement component and determining, based on the characteristic of the dry cement component, whether the dry cement component is suitable for use in a dry cement blend. In some embodiments, the commands also cause the device to transmit a message when it is determined that the dry cement component is not suitable for the dry cement blend.

A method according to the present disclosure includes receiving an output signal from each of a plurality of optical computing devices disposed in separate locations in a system for storing and conveying a bulk material or powder. The method includes processing each of the output signals from the plurality of optical computing devices with a signal processor and determining a characteristic of the stored bulk material or powder contained in a hopper based on the processing of the output signals. The method may also include transmitting a message flagging the hopper when it is determined that the bulk material or powder is not suitable for use in a dry cement blend. In some embodiments, at least one of the plurality of optical computing devices is disposed on the walls of a hopper.

While some embodiments described herein make explicit reference to a 'hopper,' it should be understood that embodiments consistent with the present disclosure may include any type of temporary storage container or bin used in the processing of bulk materials or powders, without limitation to the specific shape or form of the temporary storage container.

FIG. 1 illustrates an exemplary ICE 100 suitable for use in the optical computing devices used in systems and methods described herein. As illustrated, ICE 100 may include a plurality of alternating layers 102 and 104, such as silicon (Si) and $SiO_2$ (quartz), respectively. In general, these layers 102, 104 consist of materials whose index of refraction is high and low, respectively. Other examples might include niobia and niobium, germanium and germania, MgF, $SiO_x$, and other high and low index materials known in the art. An optical substrate 106 provides support to layers 102, 104, according to some embodiments. In some embodiments, optical substrate 106 is BK-7 optical glass. In other embodiments, optical substrate 106 may be another type of optical substrate, such as quartz, sapphire, silicon, germanium, zinc selenide, zinc sulfide, or various plastics such as polycarbonate, polymethylmethacrylate (PMMA), polyvinylchloride (PVC), diamond, ceramics, combinations thereof, and the like.

At the opposite end (e.g., opposite optical substrate 106 in FIG. 1), ICE 100 may include a layer 108 that is generally exposed to the environment of the device or installation. The number of layers 102, 104 and the thickness of each layer 102, 104 are determined from the spectral attributes acquired from a spectroscopic analysis of a characteristic of interest using a conventional spectroscopic instrument. The spectrum of interest of a given characteristic of interest typically includes any number of different wavelengths. The exemplary ICE 100 in FIG. 1 does not in fact represent any particular characteristic of interest, but is provided for purposes of illustration only. Consequently, the number of layers 102, 104 and their relative thicknesses, as shown in FIG. 1, bear no correlation to any particular characteristic of interest. Nor are layers 102, 104 and their relative thicknesses necessarily drawn to scale, and therefore should not be considered limiting of the present disclosure. Moreover, those skilled in the art will readily recognize that the materials that make up each layer 102, 104 (i.e., Si and $SiO_2$) may vary, depending on the application, cost of materials, and/or applicability of the materials to the monitored substance.

In some embodiments, the material of each layer 102, 104 can be doped or two or more materials can be combined in a manner to achieve the desired optical characteristic. In addition to solids, ICE 100 may also contain liquids and/or gases, optionally in combination with solids, in order to produce a desired optical characteristic. In the case of gases and liquids, ICE 100 can contain a corresponding vessel (not shown), which houses gases or liquids. Exemplary variations of ICE 100 may also include holographic optical elements, gratings, piezoelectric, light pipe, digital light pipe (DLP), variable optical attenuators, and/or acousto-optic elements, for example, that can create transmission, reflection, and/or absorptive properties of interest.

Layers 102, 104 exhibit different refractive indices. By properly selecting the materials of layers 102, 104, their relative thicknesses and spacing ICE 100 may be configured to selectively pass/reflect/refract predetermined fractions of electromagnetic radiation at different wavelengths. Each wavelength is given a predetermined weighting or loading factor. The thickness and spacing of layers 102, 104 may be determined using a variety of approximation methods from the spectrograph of the characteristic of interest. These methods may include inverse Fourier transform (IFT) of the optical transmission spectrum and structuring ICE 100 as the physical representation of the IFT. The approximations convert the IFT into a structure based on known materials with constant refractive indices.

The weightings that layers 102, 104 of ICE 100 apply at each wavelength are set to the regression weightings described with respect to a known equation, or data, or spectral signature. Briefly, ICE 100 may be configured to perform the dot product of the input light beam into ICE 100 and a desired loaded regression vector represented by each layer 102, 104 for each wavelength. As a result, the output light intensity of ICE 100 is related to the characteristic of interest.

Figure 2:
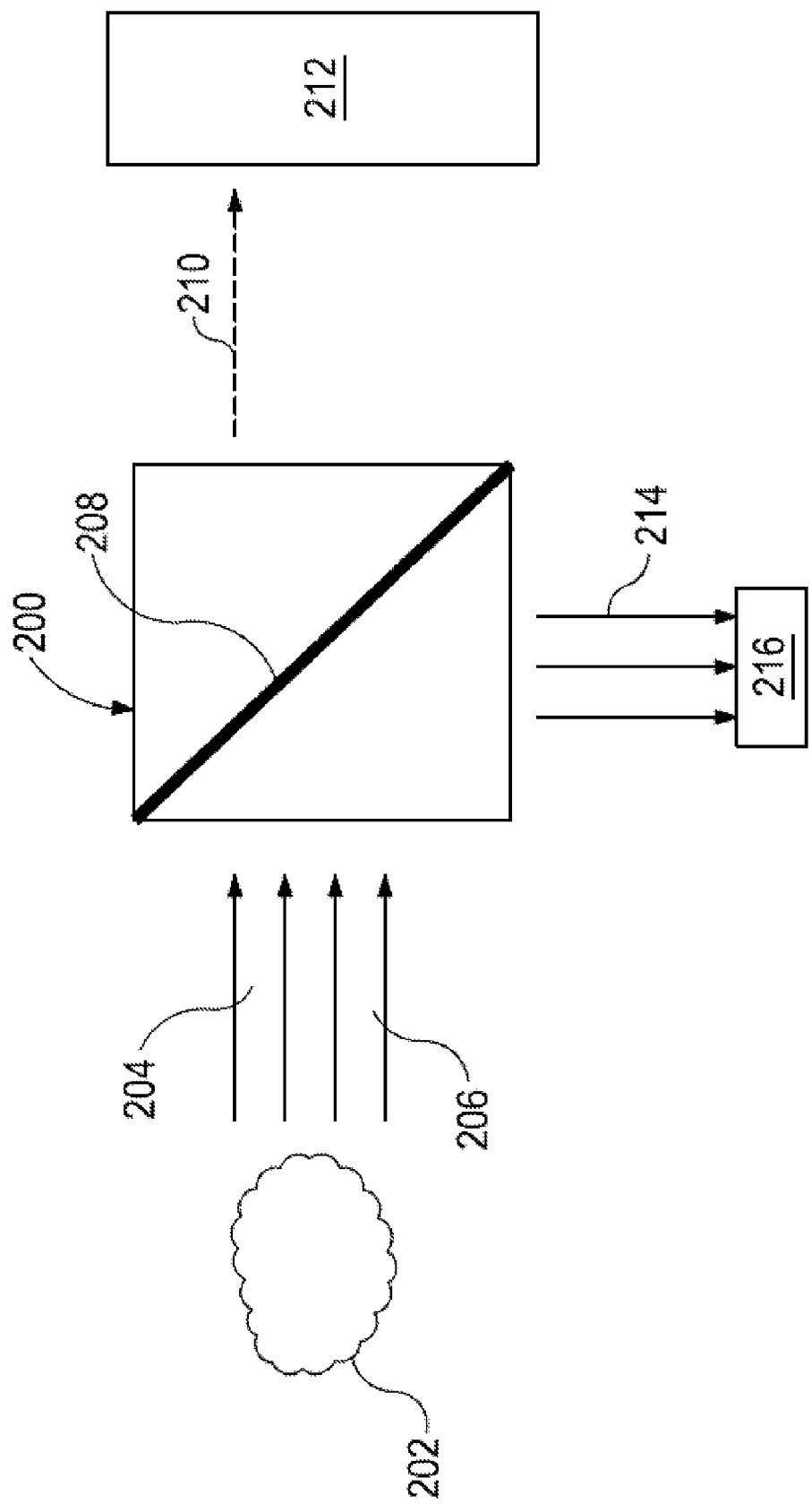
FIG. 2 illustrates a block diagram non-mechanistically illustrating how an optical computing device distinguishes electromagnetic radiation related to a characteristic of interest from other electromagnetic radiation, according to some embodiments.

FIG. 2 illustrates a block diagram that non-mechanistically illustrates how an optical computing device 200 is able to distinguish electromagnetic radiation related to a characteristic of interest from other electromagnetic radiation. As shown in FIG. 2, illumination by incident electromagnetic radiation induces an output of electromagnetic radiation from a bulk material or powder 202 (e.g., sample-interacted light), some of which is electromagnetic radiation 204 corresponding to the characteristic of interest and some of which is background electromagnetic radiation 206 corresponding to other characteristics of the bulk material or powder 202. In some embodiments, bulk material or powder 202 may include one or more characteristics of interest that may correspond to the one or more analytes of bulk material or powder 202.

Although not specifically shown, one or more processing elements may be employed in the optical computing device 200 in order to restrict the optical wavelengths and/or bandwidths of the system and thereby eliminate unwanted electromagnetic radiation existing in wavelength regions that have no importance. Such processing elements can be located anywhere along the optical train, such as directly after a light source, which provides the initial electromagnetic radiation.

Beams of electromagnetic radiation 204 and 206 impinge upon the optical computing device 200, which contains an exemplary ICE 208 therein. In the illustrated embodiment ICE 208 may produce optically interacted light, for example, transmitted optically interacted light 210, and reflected optically interacted light 214. In operation, ICE 208 may be configured to distinguish electromagnetic radiation 204 from background electromagnetic radiation 206.

Transmitted optically interacted light 210, which may be related to the characteristic of interest of the bulk material or powder 202, may be conveyed to a detector 212 for analysis and quantification. In some embodiments, detector 212 produces an output signal in the form of a voltage that corresponds to the particular characteristic of bulk material or powder 202. In at least one embodiment, the signal produced by detector 212 and the characteristic of bulk material or powder 202 (e.g., concentration of an analyte, or flow speed) may be directly proportional. In other embodiments, the relationship may be a polynomial function, an exponential function, and/or a logarithmic function. The reflected optically interacted light 214 may be related to other characteristics of the bulk material or powder 202, and can be directed away from detector 212. In alternative configurations, ICE 208 is such that reflected optically interacted light 214 relates to the characteristic of interest, and the transmitted optically interacted light 210 relates to other characteristics in the bulk material or powder 202.

In some embodiments, a second detector 216 can be present and arranged to detect the reflected optically interacted light 214. In other embodiments, second detector 216 may be arranged to detect electromagnetic radiation 204 and 206 derived from the bulk material or powder 202 or electromagnetic radiation directed toward or before the bulk material or powder 202. Without limitation, second detector 216 may be used to detect radiating deviations stemming from an electromagnetic radiation source (not shown), which provides the electromagnetic radiation (i.e., light) to the device 200. For example, radiating deviations can include such things as, but not limited to, intensity fluctuations in the electromagnetic radiation, interference fluctuations (e.g., dust or other interferences passing in front of the electromagnetic radiation source), coatings on windows included with optical computing device 200, combinations thereof, or the like. In some embodiments, a beam splitter (not shown) splits electromagnetic radiation 204 and 206, and the transmitted or reflected electromagnetic radiation can then be directed to two or more ICEs 208. That is, in such embodiments, the transmitted or reflected electromagnetic radiation passes through ICE 208, which performs the computation before it travels to detector 212.

The characteristic(s) of interest being analyzed using optical computing device 200 can be further processed and/or analyzed computationally to provide additional characterization information about bulk material or powder 202, or an analyte thereof. In some embodiments, the identification and concentration of each analyte of interest in bulk material or powder 202 can be used to predict certain physical characteristics of a resulting dry cement combination. For example, the bulk characteristics of the dry cement (e.g., reactivity, set time, and the like) can be estimated by using a combination of the properties conferred to the dry cement by each of the bulk material or powder 202 used in a cement blend. For example, the relative ratios of some of the analytes can indicate a concentration or range of concentration of cement slurry additives that should be used in preparing a cement slurry from bulk material or powder 202.

In some embodiments, knowledge of the composition and concentration of raw materials prevents a reduction in the quality of the dry cement. In some instances, mixing the stored dry cement with one or more other dry cements may achieve a desired classification or grade of dry cement. By way of non-limiting example, lime can degrade over time with exposure to carbon dioxide. Accordingly, lime is an analyte of interest that may be monitored or measured in the bulk material or powder 202, according to some embodiments.

Some embodiments use a computer algorithm to estimate the impact of a certain material quality or a certain flow characteristic in bulk material or powder 202 on the final cement composition. The algorithm may be part of an artificial neural network configured to use the concentration of each characteristic of interest in order to evaluate the overall characteristic(s) of the dry cement composition and predict the composition and/or concentration of the cement slurry additives included to provide for desired properties in resultant cement slurries. An artificial neural network can be trained using samples of predetermined characteristics of interest, and thereby generating a virtual library. As the virtual library available to the artificial neural network becomes larger, the neural network can become more capable of accurately predicting the characteristic of interest corresponding to a bulk material or powder or analyte thereof. Furthermore, with sufficient training, the artificial neural network can more accurately predict the characteristics of the dry cement combination, even in the presence of unknown analytes.

In some embodiments, data collected using the optical computing device can be archived along with data associated with operational parameters being logged at a job site. Evaluation of job performance allows improvement of future operations and the planning of remedial action, if desired. In addition, the data and information can be communicated (wired or wirelessly) to a remote location by a communication system (e.g., satellite communication or wide area network communication) for further analysis. Automated control with a long-range communication system can further facilitate the performance of remote job operations. In particular, an artificial neural network facilitates the performance of remote job operations. In other embodiments, however, remote job operations can occur under direct operator control, where the operator is not at the job site (e.g., via wireless technology).

Figure 3:
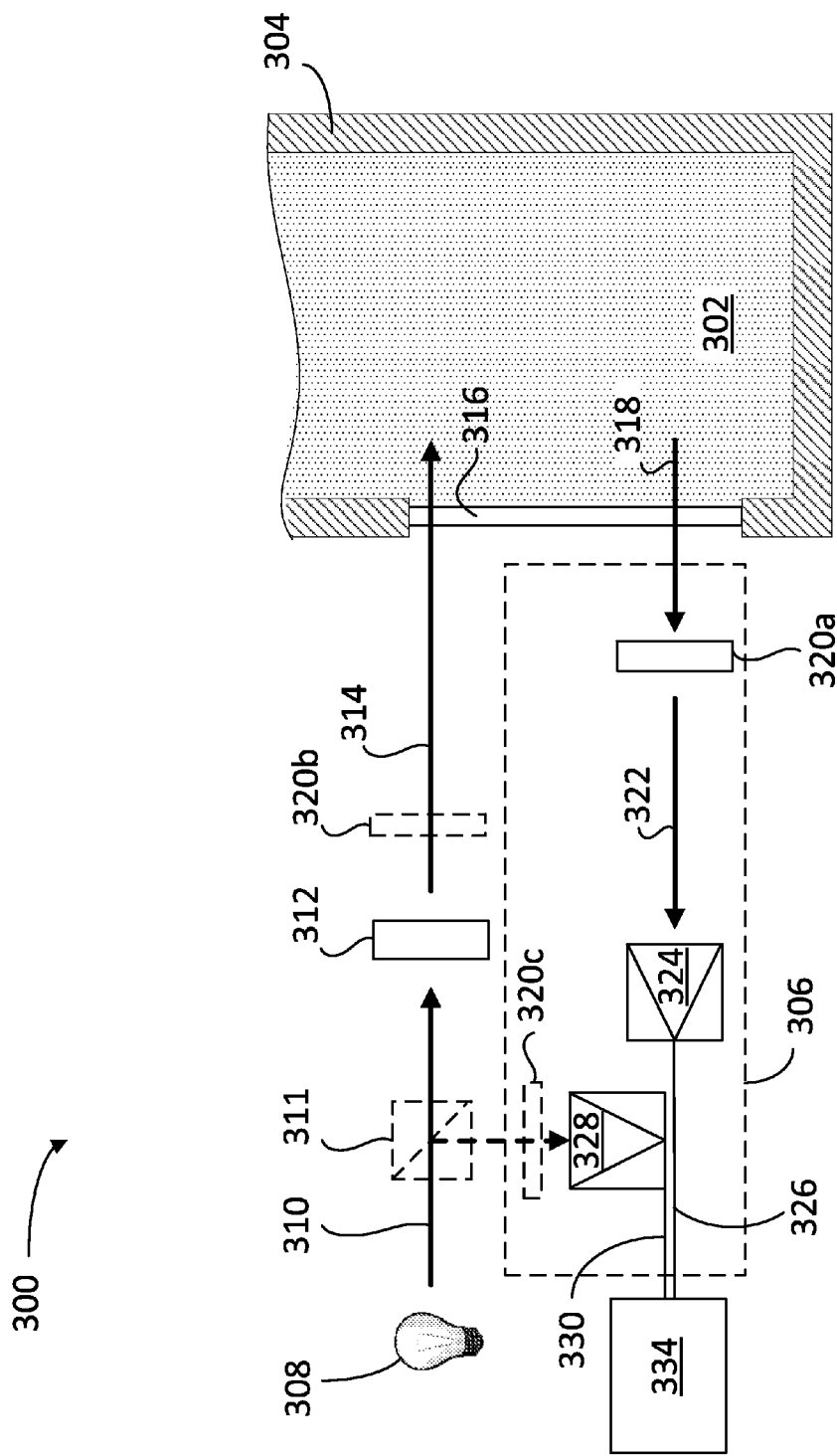
FIG. 3 illustrates an exemplary system for monitoring a dry cement present in a container, according to some embodiments.

FIG. 3 illustrates an exemplary system 300 for monitoring a bulk material or powder 302, according to one or more embodiments. In the illustrated embodiment, bulk material or powder 302 may be contained within a container 304. In at least one embodiment, container 304 may be a scale tank that actively mixes bulk material or powder 302 present therein into a cement composition while system 300 collects measurements. In at least one embodiment, container 304 may be a cup or the like of a transport unit, such as a truck or a boat. In other embodiments container 304 may be any other type of container, as generally described or otherwise defined herein. For example, container 304 may be a storage vessel or silo, or a pipeline such as a transfer tube used in the oil and gas industry, e.g., in a pneumatic conveying system.

System 300 may include at least one optical computing device 306, which may be similar in some respects to optical computing device 200 of FIG. 2. While not shown, device 306 may be housed within a casing or housing configured to substantially protect the internal components of device 306 from damage or contamination from the external environment. The housing may couple device 306 to container 304 mechanically with mechanical fasteners, threads, brazing or welding techniques, adhesives, magnets, combinations thereof or the like.

As described in detail below, optical computing device 306 may be useful in determining a particular characteristic of bulk material or powder 302 within container 304, such as determining a concentration of an analyte present within bulk material or powder 302.

Knowing at least some of the characteristics of bulk material or powder 302 may help determine the overall composition of the bulk material or powder 302. Knowing the composition of bulk material or powder 302 allows for a more accurate determination of the composition and/or concentration of cement slurry additives to use in subsequent cement slurries. In turn, the cementing operation that utilized the cement slurry mitigates premature setting or delayed setting. Further, the resultant set cement may be of higher quality because the type of and concentration of additives was tailored to the original dry cement.

In some embodiments, device 306 may include an electromagnetic radiation source 308 configured to emit or otherwise generate electromagnetic radiation 310. Electromagnetic radiation source 308 may be any device capable of emitting or generating electromagnetic radiation, as defined herein. For example, electromagnetic radiation source 308 may be a light bulb, a light emitting diode (LED), a laser, a blackbody, a photonic crystal, an X-Ray source, combinations thereof, or the like. In some embodiments, a lens 312 collects or otherwise receives electromagnetic radiation 310 and directs a beam 314 of electromagnetic radiation 310 toward bulk material or powder 302. Lens 312 may be any type of optical device configured to transmit or otherwise convey electromagnetic radiation 310 as desired. For example, lens 312 may be a normal lens, a Fresnel lens, a diffractive optical element, a holographic graphical element, a mirror (e.g., a focusing mirror), a type of collimator, or any other electromagnetic radiation-transmitting device known to those skilled in the art. Some embodiments omit lens 312 from device 306 and electromagnetic radiation source 308 conveys electromagnetic radiation 310 toward bulk material or powder 302 directly from the electromagnetic radiation source 308. In some embodiments, lens 312 includes a plurality of optical elements such as lenses and mirrors configured to direct light from electromagnetic radiation source 308 into bulk material or powder 302.

In one or more embodiments, device 306 may also include a sampling window 316 arranged adjacent to or otherwise in contact with bulk material or powder 302 for detection purposes. In some embodiments, sampling window 316 includes any one of a variety of transparent, rigid or semi-rigid materials that allow transmission of electromagnetic radiation 310 therethrough. For example, sampling window 316 may include materials such as, but not limited to, glasses, plastics, semi-conductors, crystalline materials, sapphire, polycrystalline materials, hot or cold-pressed powders, combinations thereof, or the like.

After passing through sampling window 316, electromagnetic radiation 310 impinges upon and optically interacts with bulk material or powder 302, including any analytes present within bulk material or powder 302. As a result, bulk material 302 generates and reflects optically interacted radiation 318. Those skilled in the art, however, will readily recognize that alternative variations of device 306 allow optically interacted radiation 318 to be transmitted, scattered, diffracted, absorbed, emitted, or re-radiated by and/or from the bulk material or powder 302, or one or more analytes present within the bulk material or powder 302, without departing from the scope of the disclosure.

ICEs 320a, 320b and 320c (hereinafter collectively referred to as ICEs 320) may be included in device 306. ICE 320a directs or otherwise receives optically interacted radiation 318, generated by the interaction with bulk material or powder 302. ICE devices 320 may include spectral components substantially similar to ICE 100 described above with reference to FIG. 1. Accordingly, in operation ICE 320a receives the optically interacted radiation 318 and produces modified electromagnetic radiation 322 corresponding to a particular characteristic of interest of the bulk material or powder 302. In particular, the modified electromagnetic radiation 322 is electromagnetic radiation that has optically interacted with ICE 320a and obtains an approximate mimicking of the regression vector corresponding to the characteristic of interest. In some embodiments, the characteristic of interest corresponds to bulk material or powder 302. In other embodiments, the characteristic of interest corresponds to a particular analyte found in the bulk material or powder 302. In some embodiments, the characteristic of interest may be air contained in a flow of bulk material or powder 302.

It should be noted that, while FIG. 3 depicts ICE 320a as receiving optically interacted radiation 318 from bulk material or powder 302, an ICE component may be arranged at any point along the optical train of the device 306, without departing from the scope of the disclosure. For example, in one or more embodiments, ICE 320b (as shown in dashed lines) may alternatively be arranged within the optical train prior to the sampling window 316 and equally obtain substantially the same results. In other embodiments, sampling window 316 may serve a dual purpose as both a transmission window and a substrate for one of ICEs 320 (i.e., a spectral component). In yet other embodiments, the ICE components 320 may generate modified electromagnetic radiation 322 through reflection, instead of transmission therethrough.

Moreover, while only one ICE 320a is shown in device 306, embodiments are contemplated herein which include the use of at least two ICEs 320 in device 306 configured to cooperatively determine the characteristic of interest in bulk material or powder 302. For example, two or more ICE 320 arranged in series or parallel within device 306 receive optically interacted radiation 318 thereby enhancing sensitivities and detector limits of device 306. In some embodiments, two or more ICEs 320 may be arranged on a movable assembly, such as a rotating disc or an oscillating linear array, which moves such that individual ICEs 320 are able to be exposed to or otherwise optically interact with electromagnetic radiation 310 for a distinct brief period. The two or more ICEs 320 in any of these embodiments may be associated or disassociated with the characteristic of interest in bulk material or powder 302. In other embodiments, the two or more ICEs 320 have a positive or a negative correlation with the characteristic of interest. Further, according to some embodiments, two or more ICEs 320 may have opposite correlation with the characteristic of interest. In such embodiments, while a signal in detector 324 increases with an increase in the characteristic of interest for a first ICE 320, the signal in detector 324 decreases for a second ICE 320.

In some embodiments, it may be desirable to monitor more than one characteristic of interest at a time using device 306. In such embodiments, various configurations for multiple ICEs 320 can be used, where each ICE 320 is configured to detect a particular and/or distinct characteristic of interest corresponding, for example, to bulk material or powder 302 or to an analyte in the bulk material or powder 302. Some embodiments analyze the characteristic of interest sequentially using multiple ICEs 320 interacting with a single beam of optically interacted radiation 318 reflected from or transmitted through bulk material or powder 302. For example, some embodiments include multiple ICEs 320 arranged on a rotating disc. In such embodiments, the beam of optically interacted radiation 318 interacts with individual ICEs 320 for a reduced time. Advantages of this approach can include the ability to analyze multiple characteristics of interest within bulk material or powder 302 using device 306 and the opportunity to assay additional characteristics simply by adding additional ICEs 320 to the rotating disc corresponding to those additional characteristics.

Other embodiments place multiple devices 306 at a single location along container 304, where each device 306 contains a unique ICE 320 that is configured to detect a particular characteristic of interest. In such embodiments, a beam splitter can divert a portion of the optically interacted radiation 318 reflected by, emitted from, or transmitted through the bulk material or powder 302 and into each one of devices 306. Each one of devices 306, in turn, can be coupled to a corresponding detector (e.g., detector 324) or detector array that is configured to detect and analyze an output of electromagnetic radiation from the respective optical computing device. Parallel configurations of optical computing devices can be particularly beneficial for applications that require low power inputs and/or no moving parts.

Those skilled in the art will appreciate that any of the foregoing configurations can include a series configuration in any of the present embodiments. For example, a movable housing may arrange two devices 306 in series to perform an analysis at a single location in container 304. Likewise, multiple detection stations, each containing devices 306 in parallel, can perform a similar analysis in series.

Modified electromagnetic radiation 322 generated by ICE 320a may subsequently be conveyed to the detector 324 for quantification of the signal. Detector 324 may be any device capable of detecting electromagnetic radiation, such as an optical transducer. In some embodiments detector 324 is a thermal detector such as a thermopile or photo-acoustic detector, a semiconductor detector, a piezo-electric detector, a charge coupled device (CCD) detector, a video or array detector, a split detector, a photon detector (such as a photomultiplier tube), photodiodes, combinations thereof, or the like, or other detectors known to those skilled in the art.

In some embodiments, detector 324 may be configured to produce an output signal 326 in real-time or near real-time in the form of a voltage (or current) that corresponds to the particular characteristic of interest in bulk material or powder 302. The voltage returned by detector 324 is essentially the dot product of the optical interaction of optically interacted radiation 318 with ICE 320a as a function of the concentration of the characteristic of interest. As such, output signal 326 produced by detector 324 and the characteristic of interest are related to one another. For example, output signal 326 may be directly proportional to the characteristic of interest. In other embodiments, however, the relationship may correspond to a polynomial function, an exponential function, a logarithmic function, and/or a combination thereof. In some embodiments, output signal 326 associated with ICE 320a may be negatively correlated with the characteristic of interest. Accordingly, output signal 326 decreases when the characteristic of interest increases.

In some embodiments, device 306 may include a second detector 328, which may be similar to first detector 324 in that it may be any device capable of detecting electromagnetic radiation. Similar to second detector 216 of FIG. 2, second detector 328 of FIG. 3 detects radiating deviations stemming from the electromagnetic radiation source 308. Accordingly, a beam splitter 311 (in dashes) may direct a portion of electromagnetic radiation 310 to detector 328, which may be configured to monitor radiating deviations in electromagnetic radiation source 308. In some embodiments, another ICE device 320c (shown in dashes) before detector 328 modifies the electromagnetic radiation impinging on detector 328. Undesirable radiating deviations can occur in the intensity of the electromagnetic radiation 310 due to a wide variety of reasons and potentially causing various negative effects on the output of the device 306. These negative effects can be particularly detrimental for measurements taken over a period. In some embodiments, radiating deviations can occur due to a build-up of a layer of residual material on sampling window 316. This reduces the amount and quality of light ultimately reaching first detector 324. Without proper compensation, such radiating deviations could result in false readings and output signal 326 may inaccurately relate the characteristic of interest.

To compensate for these undesirable effects, second detector 328 generates a compensating signal 330 generally indicative of the radiating deviations of the electromagnetic radiation source 308, thereby normalizing output signal 326 generated by first detector 324. As illustrated, second detector 328 may receive a portion of optically interacted radiation 318 via a beam splitter 332 in order to detect the radiating deviations. In some embodiments, second detector 328 receives electromagnetic radiation from any portion of the optical train in device 306 to detect radiating deviations, without departing from the scope of the disclosure.

In some applications, output signal 326 and compensating signal 330 may be conveyed to or otherwise received by a signal processor 334 communicably coupled to both detectors 324, 328. Signal processor 334 may be a computer including a non-transitory machine-readable medium, configured to normalize output signal 326 using compensating signal 330, in view of any radiating deviations detected by second detector 328. In some embodiments, computing output and compensating signals 326, 330 may entail computing a ratio of the two signals 326, 330. For example, the concentration or magnitude of each characteristic of interest determined using optical computing device 306 can be fed into an algorithm run by signal processor 334. The algorithm may be configured to make predictions on how the bulk material or powder 302 in combination with cement slurry additives, optionally at varying concentrations, will behave in a cement slurry.

Systems similar to that illustrated in FIG. 3 may be useful in analyzing bulk material or powders. For example, a system may include a probe that can be inserted into a dry cement for analysis of a characteristic thereof. As such, the dry cement may be contained within a container not having a device 306 connected thereto (e.g., a bag of dry cement as shipped from a distributor). Further, the dry cement may be a pile or mound of dry cement in open air.

Those skilled in the art will readily recognize that, in one or more embodiments, electromagnetic radiation derives from the bulk material or powder 302. For example, various substances naturally radiate electromagnetic radiation that is able to interact with at least one of ICE components 320. In some embodiments, for example, bulk material or powder 302 or a substance within the bulk material or powder 302 may be a blackbody radiating substance configured to radiate heat that may optically interact with at least one of ICE components 320. In other embodiments, the bulk material or powder 302 or the substance within the bulk material or powder 302 may be radioactive or chemo-luminescent and emit electromagnetic radiation that is able to interact with ICE 320. In yet other embodiments, mechanical, magnetic, electric, actuation induces electromagnetic radiation from bulk material or powder 302 or from a substance within the bulk material or powder 302. For instance, in at least one embodiment, a voltage across bulk material or powder 302 or the substance within bulk material or powder 302 induces the electromagnetic radiation. As a result, in embodiments contemplated herein the electromagnetic radiation source 308 may be omitted from the particular optical computing device.

Figure 4:
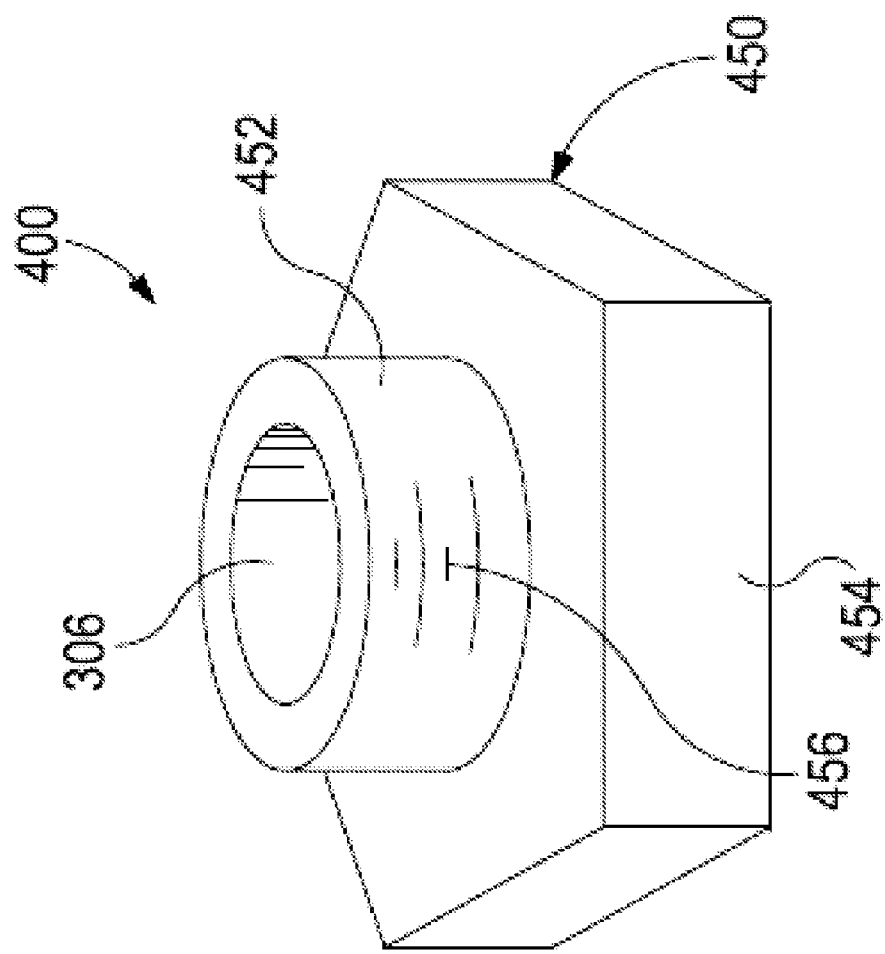
FIG. 4 illustrates an exemplary housing used to house an optical computing device, according to some embodiments.

FIG. 4 illustrates an exemplary housing 400 that may be used to house an optical computing device, according to one or more embodiments. In some embodiments, housing 400 may be mechanically coupled to container 304 using, for example, mechanical fasteners, brazing or welding techniques, adhesives, magnets, combinations thereof or the like. Housing 400 substantially protects the internal components of device 306 from damage or contamination from the external environment. Those skilled in the art, however, will readily recognize that several alternative designs and configurations of housings used to house the optical computing devices are suitable for the presently disclosed systems and methods. Indeed, housing embodiments described and disclosed herein are by way of example only, and should not limit the scope to the exemplary systems and methods disclosed herein.

As illustrated, the housing 400 may be in the general form of a bolt 450, which encloses the various components of an optical computing device, such as device 306 of FIG. 3. In one embodiment, components of the device 306 housed within housing 400 may be generally housed within a stem 452 of a bolt 450, and bolt 450 may have a hex head 454 for manual manipulation of housing 400 using, for example, a wrench or other suitable torque-generating hand tool.

In at least one embodiment, housing 400 defines external threads 456 that are compatible with corresponding mating pipe threads provided in, for example, an opening defined in container 304 (FIG. 3) that is configured to receive housing 400. A thread sealant between threads 456 and the mating pipe threads may prevent leakage of moisture or any undesirable substance through the juncture between housing 400 and the pipe. Sampling window 316 is configured to be in optical communication with bulk material or powder 302 (FIG. 3) and allows optical interaction between bulk material or powder 302 and other internal components of internally housed device 306.

Figure 5:
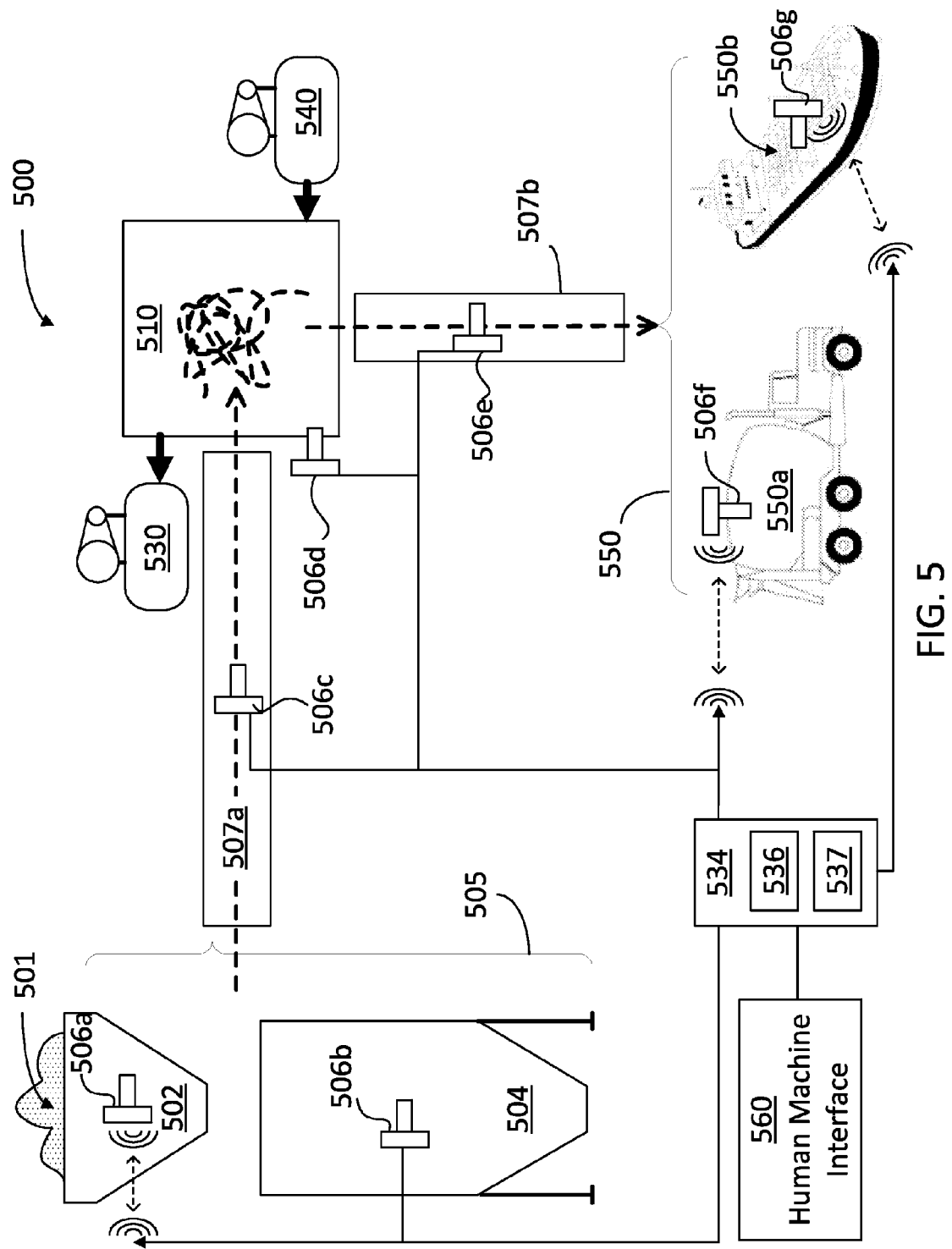
FIG. 5 illustrates a system for storing and conveying raw materials from storage containers to transportation units including an optical analysis system, according to some embodiments.

FIG. 5 illustrates a system 500 for storing and conveying raw materials from storage containers 505 to transport units 550 including an optical computing device 506, according to some embodiments. System 500 includes a storage container 505 including at least one of a hopper 502 or a storage bin 504 to store a bulk material or powder 501. Hopper 502 may be a storage container with an open top, while storage bin 504 may include a top enclosure (e.g., a tank). Bulk material or powder 501 may include any one of fly ash, silica flour, salts, or any of the materials mentioned above in a dry cement combination, including cement additives in powder form. Other dry materials 501 besides dry cement that may be transferred in hopper 502 include salt, lime, sand, POZ-MIX®, and the like. In some embodiments of system 500, hopper 502 conveys different materials through transfer tube 507a into scale tank 510, sequentially. Transfer tube 507a conveys bulk material or powder 501 from any one of storage containers 505 (including storage bin 504) to a scale tank 510. In some embodiments, a pump 530 creates a negative air pressure in the scale tank to generate a flow of bulk material or powder 501, thus 'pulling' bulk material or powder 501 through transfer tube 507a. In other embodiments, the bulk material may gravity flow from 505 through 507a into 510. Scale tank 510 receives raw materials from different storage containers 505 such as hopper 502 and storage bin 504 and forms a mix, such as dry cement. The mixture may be developed by ribbon blending, jets, multiple transfers and such, with 506d determining when the mixture is satisfactorily homogeneous. Transfer tube 507b conveys the mixed materials to a truck 550a or a ship 550b for shipping the blended materials (e.g., dry cement) to a deployment location. Transfer tubes 507a and 507b will be referred hereinafter to as transfer tubes 507. In some embodiments, transfer tube 507b includes a flow of the bulk material or powder mixed with air, the air provided by an air pump 540 creating a positive air pressure in the scale tank, thus 'pushing' bulk material or powder 501 through transfer tube 507b. In some embodiments, the role of pump 530 and air compressor 540 may be reversed, so that an air compressor 540 'pushes' raw material from storage containers 505 into scale tank 510. Or in some embodiments pump 530 may be used to 'pull' a material mix from scale tank 510 to transport units 550a (e.g., a truck) and 550b (e.g., a ship). Transport units 550a and 550b will be referred hereinafter to as transport units 550.

In some embodiments, it may be desirable to know in real time that the correct material is in any one of storage containers 505, or in any one of transfer tubes 507, scale tank 510, or even within transport units 550. Accordingly, system 500 includes a plurality of optical computing devices disposed in different locations. Optical computing device 506a is located within hopper 502. Optical computing device 506b is located within storage bin 504. Optical computing device 506c is located within transfer tube 507a. Optical computing device 506d is located within scale tank 510. Optical computing device 506e is located within transfer tube 507b. Optical computing device 506f is located within truck 550a, and optical computing device 506g is located within ship 550b. Optical computing devices 506a-g will be collectively referred to hereinafter as optical computing devices 506. In some embodiments, at least one of optical computing devices 506 may be as optical computing device 306 in FIG. 3.

System 500 also includes a signal processor 534 having a processor circuit 536 and a memory circuit 537 storing commands. Signal processor 534 may be similar to signal processor 334 of FIG. 3. When executed by processor circuit 536 the commands cause signal processor 534 to perform a method including receiving a first signal from a first optical computing device 506a at a first location in system 500. The commands may also cause signal processor 534 to perform the step of receiving a second signal from a second optical computing device 506b at a second location in system 500. The first and second location in system 500 may be any one of storage containers 505, transfer tubes 507, scale tank 510, or even transport units 550. In that regard, optical computing devices 506 and signal processor 534 may exchange data and signals via a wire connection, or a wireless connection. The first and second signal may result from a light interacted with a bulk material or powder 501, and at least one of the first and second signals results from an electromagnetic radiation modified by an ICE. In some embodiments, the commands further cause signal processor 534 to perform the step of determining from the first and second signal a characteristic of the bulk material or powder, or of the flow of the bulk material or powder. More generally, processor circuit 536 may execute commands stored in memory circuit 537 that cause signal processor 534 to perform at least one of the steps in any method consistent with the present disclosure. A Human Machine Interface (HMI) 560 may be coupled to signal processor 534, and be configured to monitor the operation of system 500 by a human operator. Accordingly, HMI 560 may issue warnings, alert messages, or alarms, based on the data provided by signal processor 534 upon collecting signals from each of optical computing devices 506.

Optical computing devices 506 enable real time monitoring and detection of various compounds in most any phase, including powders, liquids and slurries. For example, an ICE in any one of optical computing devices 506 (e.g., ICE 100 in FIG. 1) may identify cement powder ingredients used in dry cement compositions. Monitoring and detecting the chemical composition (or at least key ingredients) through optical computing devices 506 enables identification and verification of bulk material or powder 501 in hopper 502, in storage bin 504 or in one of the transfer tubes 507a and 507b. Optical computing devices 506 also enable detection of the condition of bulk material or powder 501. For example, optical computing devices 506 may determine when excessive moisture or decomposition occurs in storage or while conveyed in and out of scale tank 510. A window or a probe provides optical communication between optical computing devices 506 and storage containers 505, transfer tubes 507, or transport units 550. The window may be similar to window 316 of FIG. 3, and the probe may include a waveguide device to transmit electromagnetic radiation, such as an optical fiber.

Accordingly, methods and systems consistent with the present disclosure provide fast identification of dry materials contained in a storage bin, a hopper, or a pneumatic conveyor. System 500 also includes a programmed control system with alarms and reporting to prevent contamination of bulk materials or powders from interconnecting piping with different storage bins, or from different materials delivered to the storage bin or hopper. Accordingly, system 500 enhances the confidence level for adding to a blend the correct materials in their suitable condition. Accordingly, embodiments consistent with the present disclosure decrease the likelihood of ruined bulk material or powder batches being disposed of. Thus decreasing waste disposal costs and material costs to the plant. Methods and systems consistent with the present disclosure also decrease the likelihood of compromised bulk material blends: arriving on location, mixing in a blend, and pumped into a borehole. This also decreases the cost of poor quality, and the likelihood of downtime due to test and repair of damaged structures. Furthermore, embodiments consistent with the present disclosure decrease occurrence of equipment damage due to flash setting in the mixing and pumping system and/or poor slurry mixability.

Figure 6:
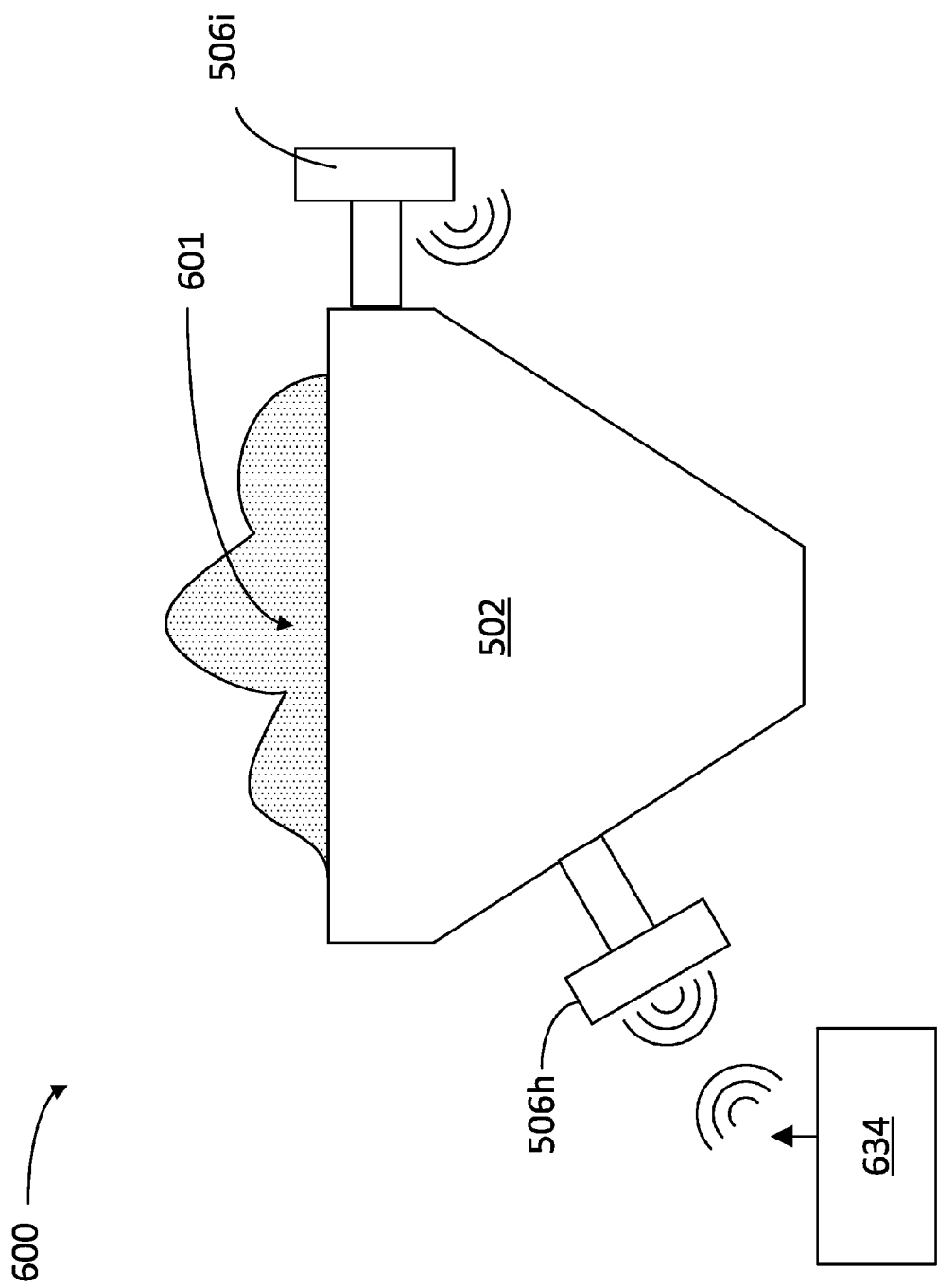
FIG. 6 illustrates a hopper including an optical analysis system to identify material type and condition of a bulk material or powder, according to some embodiments.

FIG. 6 illustrates an exemplary system 600 that may include a hopper 502 and one or more optical computing devices 506h and 506i (hereinafter referred to as optical computing devices 506), according to some embodiments. As illustrated, optical computing devices 506 may be coupled to a sidewall of hopper 502 at different locations and otherwise in optical communication with a bulk material or powder 601 disposed within the hopper 502. In at least one embodiment, the bulk material or powder 601 may be a dry cement composition and the system 600 may be configured to detect one or more characteristics of the bulk material or powder 601, such as the chemical composition, material type, and current condition of the bulk material or powder 601.

The system 600 may further include a signal processor 634 communicably coupled to optical computing devices 506 and configured to receive a detection signal therefrom and provide an output signal indicative of the one or more characteristics of the bulk material or powder 601. In some embodiments, hopper 502 may be a mobile container, so that optical analysis system 400 communicates wirelessly with signal processor 634. Hopper 502 may receive different bulk materials or powders 601 sequentially, so that the period that materials 601 remain inside hopper 502 is relatively low. For this reason, the likelihood of contamination between different bulk materials or powders 601 used in the past on the same hopper may be high. In some embodiments, optical computing devices 506 avoid the occurrence of error and mishandling of the components of a dry cement prior to mixing. For example, optical computing device 506 may be able to determine that the material in hopper 502 has been improperly labeled or misplaced, thus sending an alert signal through signal processor 634 to an HMI (e.g., HMI 560, cf. FIG. 5).

FIG. 7 illustrates a flowchart including steps in a method 700 for identification of material type and condition in a bulk material or powder contained in a hopper, according to some embodiments. Embodiments consistent with method 700 include a hopper in a system for storing and conveying materials from containers to transport units (e.g., hopper 502, and system 500, cf. FIGS. 5 and 6). Accordingly, system for storing and conveying materials in methods consistent with method 700 may include at least one optical analysis system that has an ICE, a detector, and a signal processor (e.g., detectors 324 and 328, and signal processor 334, cf. FIG. 3, and optical analysis system 400, cf. FIG. 4). Some embodiments include the optical analysis system mounted on the hopper to determine a characteristic of a bulk material or powder (e.g., optical analysis system 400 and bulk material or powder 601, cf. FIG. 6). In some instances, at least one of the steps in method 700 includes using computers and optionally artificial neural networks. For example, in some embodiments at least one or more of the steps in method 700 include a signal processing circuit executing commands stored in a memory circuit, and coupled to an HMI (e.g., signal processor 534, processing circuit 536, memory circuit 537, and HMI 560, cf. FIG. 5). Steps in methods consistent with the present disclosure may include at least any of the steps in method 700, performed in any order. Furthermore, embodiments consistent with the present disclosure may include one or more of the steps in method 700 performed overlapping in time, or simultaneous in time.

Step 710 includes optically interacting a bulk material or powder contained in a hopper with an ICE. Accordingly, the ICE may be configured to modify an electromagnetic radiation that is interacted with the bulk material or powder according to a characteristic of the bulk material or powder. Accordingly, the ICE produces a modified electromagnetic radiation correlated to the characteristic of the bulk material or powder. In some embodiments, step 710 includes providing an electromagnetic radiation to be interacted with the bulk material or powder in the hopper. In some embodiments, step 710 includes providing an electromagnetic radiation source, and in some embodiments step 710 may include using an electromagnetic radiation generated internally in the hopper (e.g., by a flare sparked inside the hopper). Further, in some embodiments step 710 includes using a natural source of electromagnetic radiation from the sun or any other natural source. Step 720 includes detecting the modified interacted electromagnetic radiation resulting from the optical interaction of the bulk material or powder with the ICE. In some embodiments, step 720 includes receiving the modified electromagnetic radiation in the detector. In some embodiments, step 720 includes processing a detector signal with the signal processor. Processing the detector signal may include finding a time correlation between signals provided by at least two optical measurement systems disposed at selected locations in the hopper. In some embodiments, step 720 includes taking time-lapsed measurements of the dry cement composition with a single optical computing device and comparing the resulting signals to determine how the characteristic of the dry cement composition changed over time.

Step 730 includes producing an output signal being correlated to the characteristic of the bulk material or powder. In some embodiments, step 730 includes determining the characteristic of the stored bulk material or powder based on the detector signal. The characteristic of the bulk material or powder may be an identification of the chemical composition of the bulk material or powder, a purity value (e.g., 98%, 99% concentration or higher), a contaminant concentration value, a moisture concentration value, a particle size value, a homogeneity, and an air content, among others. In some embodiments, determining a particle size is useful in determining a quality of the bulk material or powder stored in the container within the system for storing and conveying raw materials. For example, larger particle sizes can lead to reduced strength set cements and may therefore benefit from a strengthening cement slurry additive (e.g., fibers or other resilient particles). Conversely, bulk materials or powders with smaller particle sizes typically use more water to hydrate completely because of the increased surface area relative to weight.

Step 740 includes determining whether the bulk material or powder is suitable for a blending process (e.g., for a dry cement blend). In some embodiments, step 740 includes comparing the characteristic of the stored bulk material or powder with a database. A database including ranges of acceptable values for the characteristic of the bulk material or powder may be stored in the memory circuit of the signal processor. In some embodiments, step 740 includes determining whether there is a discrepancy between the value of the characteristic of the bulk material or powder and the database. Accordingly, step 740 may include determining that the value of the characteristic obtained is outside the range of acceptable values listed in the database for the specific characteristic of the bulk material or powder. When the bulk material or powder is suitable for a blending process according to step 740, steps 710 through 730 may be repeated in method 700.

Step 750 includes transmitting an alert when the bulk material or powder is not suitable for a blending process according to step 740. In some embodiments, step 750 includes alerting an operator and transmitting a message flagging the hopper in the event that multiple hoppers carrying different materials are being used. Accordingly, step 750 may include determining that the characteristic obtained is outside the range of acceptable values listed in the database for the specific characteristic of the bulk material or powder. In some embodiments, step 750 includes adjusting a flow parameter in a transfer tube in the system for storing and conveying materials according to a value obtained from the light interacted with the bulk material or powder in the hopper. This may be the case when the hopper feeds the bulk material or powder to a transfer tube in a system for storing and conveying materials.

When the system detects a discrepancy in the material contained in the hopper versus the criteria stored in the system, some embodiments may shut down the transfer process from the hopper to the scale tank. For example, a valve in a transfer tube between the hopper and the scale tank may be closed. Some embodiments may issue a warning (pop-up) on the screen of the HMI, stating what the discrepancy is, and that the operator may address before allowing continued operation of the material transfer from the hopper to the scale tank. In some embodiments, the HMI is configured to record the alert event and the operator's response to the warning in the system for later reporting.

It is recognized that the various embodiments herein directed to computer control and artificial neural networks, including various blocks, modules, elements, components, methods, and algorithms, can be implemented using computer hardware, software, combinations thereof, and the like. To illustrate this interchangeability of hardware and software, various illustrative blocks, modules, elements, components, methods and algorithms have been described generally in terms of their functionality. Whether such functionality is implemented as hardware or software will depend upon the particular application and any imposed design constraints. For at least this reason, it is to be recognized that one of ordinary skill in the art can implement the described functionality in a variety of ways for a particular application. Further, various components and blocks can be arranged in a different order or partitioned differently, for example, without departing from the scope of the embodiments expressly described.

Computer hardware used to implement the various illustrative blocks, modules, elements, components, methods, and algorithms described herein can include a processor configured to execute one or more sequences of instructions, programming stances, or code stored on a non-transitory, computer-readable medium. The processor can be, for example, a general purpose microprocessor, a microcontroller, a digital signal processor, an application specific integrated circuit, a field programmable gate array, a programmable logic device, a controller, a state machine, a gated logic, discrete hardware components, an artificial neural network, or any like suitable entity that can perform calculations or other manipulations of data. In some embodiments, computer hardware can further include elements such as, for example, a memory (e.g., random access memory (RAM), flash memory, read only memory (ROM), programmable read only memory (PROM), erasable read only memory (EPROM)), registers, hard disks, removable disks, CD-ROMs, DVDs, or any other like suitable storage device or medium.

Executable sequences described herein can be implemented with one or more sequences of code contained in a memory. In some embodiments, such code can be read into the memory from another machine-readable medium. Execution of the sequences of instructions contained in the memory can cause a processor to perform the process steps described herein. One or more processors in a multi-processing arrangement can also be employed to execute instruction sequences in the memory. In addition, hard-wired circuitry can be used in place of or in combination with software instructions to implement various embodiments described herein. Thus, the present embodiments are not limited to any specific combination of hardware and/or software.

As used herein, a machine-readable medium will refer to any medium that directly or indirectly provides instructions to a processor for execution. A machine-readable medium can take on many forms including, for example, non-volatile media, volatile media, and transmission media. Non-volatile media can include, for example, optical and magnetic disks. Volatile media can include, for example, dynamic memory. Transmission media can include, for example, coaxial cables, wire, fiber optics, and wires that form a bus. Common forms of machine-readable media can include, for example, floppy disks, flexible disks, hard disks, magnetic tapes, other like magnetic media, CD-ROMs, DVDs, other like optical media, punch cards, paper tapes and like physical media with patterned holes, RAM, ROM, PROM, EPROM, and flash EPROM.

Embodiments disclosed herein include:

A. A method that includes optically interacting a bulk material or powder contained in a hopper with an integrated computational element ("ICE") configured to modify an electromagnetic radiation according to a characteristic of the bulk material or powder, detecting the modified electromagnetic radiation with a detector, producing an output signal with a signal processor, the output signal being correlated to a characteristic of the bulk material or powder, determining whether the bulk material or powder is suitable for a blending process, and transmitting an alert when it is determined that the bulk material or powder is not suitable for the blending process, wherein the bulk material or powder comprises at least one of a dry cement or a dry cement component.

B. A device that includes a processor circuit, and a memory circuit storing commands, which when executed by the processor circuit cause the device to perform a method comprising receiving a first signal from a first optical computing device at a first location in a system for storing and conveying materials, receiving a second signal from a second optical computing device at a second location in the system for storing and conveying materials, wherein at least one of the first and second signal result from an electromagnetic radiation interacted with a dry cement component contained in a hopper, and at least one of the first and second signals results from an electromagnetic radiation modified by an Integrated Computational Element (ICE) according to a characteristic of the dry cement component, determining whether the dry cement component is suitable for use in a dry cement blend, and transmitting a message when it is determined that the dry cement component is not suitable for the dry cement blend.

C. A method that includes receiving an output signal from each of a plurality of optical computing devices disposed in separate locations in a system for storing and conveying a bulk material or powder, processing each of the output signals from the plurality of optical computing devices with a signal processor, determining a characteristic of the bulk material or powder contained in a hopper based on the processing of the output signals, and transmitting a message flagging the hopper when it is determined that the bulk material or powder is not suitable for use in a dry cement blend, wherein at least one of the plurality of optical computing devices is disposed on the walls of the hopper.

Each of embodiments A, B, and C may have one or more of the following additional elements in any combination: Element 1: wherein the characteristic of the bulk material or powder is at least one of a moisture content or a contaminant. Element 2: wherein producing an output signal being correlated to the characteristic of the bulk material or powder comprises determining a concentration of fines. Element 3: further comprising triggering an alarm when it is determined that the bulk material or powder is not suitable for use in a dry cement blend. Element 4: further comprising transmitting a message clearing the hopper when it is determined that the bulk material or powder is suitable for use in a dry cement blend. Element 5: wherein determining whether the bulk material or powder is suitable for a blending process comprises comparing, in a database, the characteristic of the sample with a range of acceptable values. Element 6: wherein transmitting an alert when it is determined that the bulk material or powder is not suitable for the blending process comprises alerting that the bulk material or powder has been wrongly labeled or misplaced.

Element 7: wherein the memory circuit further comprises a database having a range of acceptable values for the characteristic of the dry cement component, and the commands further cause the device to perform the step of comparing the value of the characteristic of the dry cement component with the database. Element 8: wherein the characteristic of the dry cement component comprises a particle size. Element 9: wherein the characteristic of the dry cement component comprises a humidity value and a contamination material content. Element 10: wherein at least one of the first and second locations include a storage bin storing a second dry cement component. Element 11: wherein at least one of the first and second locations include a transfer tube in a pneumatic conveyor to transport a second dry cement component. Element 12: wherein the memory circuit further comprises commands that cause the device to perform the step of triggering an alarm when it is determined that the dry cement component is not suitable for use in a dry cement blend. Element 13: further comprising a wireless communication circuit to receive the at least one of the first and second signals from an optical computing device located in the hopper. Element 14: wherein the memory circuit further comprises commands to cause the device to perform the step of adjusting a flow parameter in a transfer tube in the system for storing and conveying materials according to a value obtained from the light interacted with the bulk material or powder in the hopper. Element 15: wherein determining whether the dry cement component is suitable for use in a dry cement blend comprises determining a concentration of fines. Element 16: further comprising commands to cause the device to perform the step of transmitting a message clearing the hopper when it is determined that the bulk material or powder is suitable for use in a dry cement blend.

Element 17: further comprising producing an output signal correlated to the characteristic of the bulk material or powder with one or more of the plurality of optical computing devices, and determining a concentration of fines based on the output signal. Element 18: wherein determining a characteristic of the bulk material or powder comprises determining at least one of a moisture content or a contaminant. Element 19: further comprising associating a location in the system with the characteristic of the bulk material or powder for at least the optical analysis system disposed on the walls of the hopper. Element 20: further comprising triggering an alarm when it is determined that the bulk material or powder in the hopper is not suitable for use in a dry cement blend. Element 21: further comprising transmitting a message when it is determined that the bulk material or powder is suitable for use in a dry cement blend.

The exemplary embodiments described herein are well adapted to attain the ends and advantages mentioned as well as those that are inherent therein. The particular embodiments disclosed above are illustrative only, as the exemplary embodiments described herein may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope and spirit of the present invention. The invention illustratively disclosed herein suitably may be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces. If there is any conflict in the usages of a word or term in this specification and one or more patent or other documents that may be incorporated herein by reference, the definitions that are consistent with this specification should be adopted.

As used herein, the phrase "at least one of" preceding a series of items, with the terms "and" or "or" to separate any of the items, modifies the list as a whole, rather than each member of the list (i.e., each item). The phrase "at least one of" does not require selection of at least one item; rather, the phrase allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

The invention claimed is:
1. A method comprising:
optically interacting a bulk material or powder contained in a hopper with an integrated computational element ("ICE") configured to modify an electromagnetic radiation according to a characteristic of the bulk material or powder;
detecting the modified electromagnetic radiation with a detector;
producing an output signal with a signal processor, the output signal being correlated to a characteristic of the bulk material or powder;
determining whether the bulk material or powder is suitable for a blending process; and
transmitting an alert when it is determined that the bulk material or powder is not suitable for the blending process, wherein the bulk material or powder comprises at least one of a dry cement or a dry cement component.

2. The method of claim 1, wherein the characteristic of the bulk material or powder is at least one of a moisture content or a contaminant.

3. The method of claim 1, wherein producing an output signal being correlated to the characteristic of the bulk material or powder comprises determining a concentration of fines.

4. The method of claim 1, further comprising triggering an alarm when it is determined that the bulk material or powder is not suitable for use in a dry cement blend.

5. The method of claim 1, further comprising transmitting a message clearing the hopper when it is determined that the bulk material or powder is suitable for use in a dry cement blend.

6. The method of claim 1, wherein determining whether the bulk material or powder is suitable for a blending process comprises comparing, in a database, the characteristic of the bulk material or powder with a range of acceptable values.

7. The method of claim 1, wherein transmitting an alert when it is determined that the bulk material or powder is not suitable for the blending process comprises alerting that the bulk material or powder has been wrongly labeled or misplaced.

8. A device comprising:
 a processor circuit; and
 a memory circuit storing commands, which when executed by the processor circuit cause the device to perform a method comprising:
  receiving a first signal from a first optical computing device at a first location in a system for storing and conveying materials;
  receiving a second signal from a second optical computing device at a second location in the system for storing and conveying materials, wherein at least one of the first and second signals result from an electromagnetic radiation interacted with a dry cement component contained in a hopper, and at least one of the first and second signals results from an electromagnetic radiation modified by an Integrated Computational Element (ICE) according to a characteristic of the dry cement component;
  determining whether the dry cement component is suitable for use in a dry cement blend; and
  transmitting a message when it is determined that the dry cement component is not suitable for the dry cement blend.

9. The device of claim 8, wherein the memory circuit further comprises a database having a range of acceptable values for the characteristic of the dry cement component, and the commands further cause the device to perform the step of comparing the value of the characteristic of the dry cement component with the database.

10. The device of claim 8, wherein the characteristic of the dry cement component comprises a particle size.

11. The device of claim 8, wherein the characteristic of the dry cement component comprises a humidity value and a contamination material content.

12. The device of claim 8, wherein at least one of the first and second locations includes a storage bin storing a second dry cement component.

13. The device of claim 8, wherein at least one of the first and second locations includes a transfer tube in a pneumatic conveyor to transport a second dry cement component.

14. The device of claim 8, wherein the memory circuit further comprises commands that cause the device to perform the step of triggering an alarm when it is determined that the dry cement component is not suitable for use in a dry cement blend.

15. The device of claim 8, further comprising a wireless communication circuit to receive the at least one of the first and second signals from an optical computing device located in the hopper.

16. The device of claim 8, wherein the memory circuit further comprises commands to cause the device to perform the step of adjusting a flow parameter in a transfer tube in the system for storing and conveying materials according to a value obtained from the light interacted with the bulk material or powder in the hopper.

17. The device of claim 8, wherein determining whether the dry cement component is suitable for use in a dry cement blend comprises determining a concentration of fines.

18. The device of claim 8, further comprising commands to cause the device to perform the step of transmitting a message clearing the hopper when it is determined that the bulk material or powder is suitable for use in a dry cement blend.

19. A method comprising:
 receiving an output signal from each of a plurality of optical computing devices disposed in separate locations in a system for storing and conveying a bulk material or powder;
 processing each of the output signals from the plurality of optical computing devices with a signal processor;
 determining a characteristic of the bulk material or powder contained in a hopper based on the processing of the output signals;
 transmitting a message flagging the hopper when it is determined that the bulk material or powder is not suitable for use in a dry cement blend, wherein at least one of the plurality of optical computing devices is disposed on the walls of the hopper;
 producing an output signal correlated to the characteristic of the bulk material or powder with one or more of the plurality of optical computing devices; and
 determining a concentration of fines based on the output signal.

20. The method of claim 19, wherein determining a characteristic of the bulk material or powder comprises determining at least one of a moisture content or a contaminant.

21. The method of claim 19, further comprising associating a location in the system with the characteristic of the bulk material or powder for at least one optical analysis system disposed on the walls of the hopper.

22. The method of claim 19, further comprising triggering an alarm when it is determined that the bulk material or powder in the hopper is not suitable for use in a dry cement blend.

23. The method of claim 19, further comprising transmitting a message when it is determined that the bulk material or powder is suitable for use in a dry cement blend.

* * * * *